United States Patent
Sato

(10) Patent No.: US 8,391,969 B2
(45) Date of Patent: Mar. 5, 2013

(54) BODY COMPOSITION MONITOR, MEASUREMENT RESULT OUTPUT METHOD, AND MEASUREMENT RESULT OUTPUT PROGRAM PRODUCT

(75) Inventor: Tetsuya Sato, Nishinomiya (JP)

(73) Assignee: Omron Healthcare Co., Ltd., Kyoto-shi (JP)

( * ) Notice: Subject to any disclaimer, the term of this patent is extended or adjusted under 35 U.S.C. 154(b) by 0 days.

(21) Appl. No.: 13/207,985

(22) Filed: Aug. 11, 2011

(65) Prior Publication Data

US 2011/0295145 A1 Dec. 1, 2011

Related U.S. Application Data

(63) Continuation of application No. PCT/JP2009/071330, filed on Dec. 22, 2009.

(30) Foreign Application Priority Data

Mar. 27, 2009 (JP) ................................. 2009-080170

(51) Int. Cl.
*A61B 5/05* (2006.01)

(52) U.S. Cl. ...................................................... 600/547

(58) Field of Classification Search .................... 600/547
See application file for complete search history.

(56) References Cited

U.S. PATENT DOCUMENTS

| | | | |
|---|---|---|---|
| 2004/0220492 A1 | 11/2004 | Kodama et al. | |
| 2005/0209528 A1 | 9/2005 | Sato et al. | |

FOREIGN PATENT DOCUMENTS

| JP | A-2001-204705 | 7/2001 |
|---|---|---|
| JP | A-2004-81621 | 3/2004 |
| JP | A-2004-329412 | 11/2004 |
| JP | A-2004-344518 | 12/2004 |
| JP | A-2005-110962 | 4/2005 |
| JP | A-2005-261488 | 9/2005 |

OTHER PUBLICATIONS

International Search Report issued in International Application No. PCT/JP2009/071330 on Apr. 6, 2010 (with translation).

*Primary Examiner* — Brian Szmal
(74) *Attorney, Agent, or Firm* — Oliff & Berridge, PLC

(57) ABSTRACT

A body composition monitor calculates a body composition value of a whole body and a body composition value by site of a user using a plurality of electrodes, and calculates a site ratio representing a ratio of the body composition value by site with respect to the body composition value of the whole body. A process of outputting ratio information (site ratio and/or evaluation index of site ratio) related to the calculate site ratio is then carried out.

11 Claims, 13 Drawing Sheets

BODY COMPOSITION MONITOR, MEASUREMENT RESULT OUTPUT METHOD, AND MEASUREMENT RESULT OUTPUT PROGRAM PRODUCT

TECHNICAL FIELD

The present invention relates to body composition monitors, measurement result output methods, and measurement result output program products, and in particular, to a body composition monitor capable of calculating a body composition of a whole body and a body composition by site through a bioelectrical impedance method, a measurement result output method, and a measurement result output program product.

BACKGROUND ART

A conventional body composition monitor includes the following.

Japanese Unexamined Patent Publication No. 2004-81621 (Patent Document 1) describes determining a proportion age from a correlation of a ratio of a body trunk fat mass with respect to a lower limb fat mass and the age, determining a physical strength age from the correlation of the ratio of a weight of the upper half of the body with respect to a lower limb muscle mass and the age, and determining the body build physical strength of the user based on such determined data.

Japanese Unexamined Patent Publication No. 2005-110962 (Patent Document 2) describes determining a body type from a body build index number and a body composition index.

Japanese Unexamined Patent Publication No. 2004-344518 (Patent Document 3) describes determining the level of the muscle mass from the muscle mass/height", and calculating the body build age level.

Japanese Unexamined Patent Publication No. 2005-261488 (Patent Document 4) describes displaying a fluctuation degree in the ratio of the muscle percentage and the fat percentage for every site.

Patent Document 1: Japanese Unexamined Patent Publication No. 2004-81621
Patent Document 2: Japanese Unexamined Patent Publication No. 2005-110962
Patent Document 3: Japanese Unexamined Patent Publication No. 2004-344518
Patent Document 4: Japanese Unexamined Patent Publication No. 2005-261488

SUMMARY OF THE INVENTION

Problems to be Solved by the Invention

As described above, the conventional body composition monitor not only calculates and displays the body composition but also calculates and displays various indices from the body composition.

However, in the body composition monitor described in Japanese Unexamined Patent Publication No. 2005-110962 and Japanese Unexamined Patent Publication No. 2004-344518 (Patent Documents 2, 3), the average body type and body build age level of the body are calculated and displayed in comparison with the subject group of the database. Therefore, the user can recognize his or her position from the displayed information.

In contrast, Japanese Unexamined Patent Publication No. 2004-81621 (Patent Document 1) and Japanese Unexamined Patent Publication No. 2005-261488 (Patent Document 4) describe using the ratio of the body composition value at two different sites of the user himself/herself or the ratio of two different types of body composition values of the user himself/herself to calculate the index.

However, there is a drawback in that whether there is bias in covering for every site of the body composition such as fat and muscle of the user himself/herself cannot be recognized with such indices.

The present invention has been made in view of solving the above problem, and an object thereof is to provide a body composition monitor capable of presenting to the user whether there is bias in covering of the body composition for every site, a measurement result output method, and a measurement result output program product.

Means for Solving the Problem

In accordance with one aspect of the present invention, a body composition monitor includes a plurality of electrodes to be brought into contact with a surface of a body of a user; a first calculating portion for calculating a body composition value of a whole body and a body composition value by site of the user using the electrodes; a second calculating portion for calculating a site ratio representing a ratio of the body composition value by site with respect to the body composition value of the whole body; an evaluating portion for calculating a site evaluation index representing an evaluation index related to the calculated site ratio; and an output processing portion for displaying information including the site evaluation index on a display unit.

The site evaluation index includes a high and low level representing a height of the site ratio. The output processing portion displays a human body mark schematically showing a human body on the display unit and also displays a position in the human body mark corresponding to a site where the calculated high and low level is higher than average or a site where the calculated high and low level is lower than average of the site so as to be identifiable from other positions.

The output processing portion preferably displays on the display unit whole body information related to the body composition value of the whole body in association with the site evaluation index.

The whole body information preferably includes at least one of the body composition value of the whole body and an evaluation index of the body composition value of the whole body in a physical attribute including sex of the user.

The output processing portion preferably displays the calculated site ratio on the display unit.

The body composition monitor preferably further includes a storage unit for storing in advance specific information for specifying a relationship of each high and low level representing a height of the site ratio and the site ratio for every physical attribute of a measurer. The evaluating portion calculates the high and low level corresponding to the calculated site ratio based on the specific information, the physical attribute of the user, and the calculated site ratio.

The specific information preferably includes at least one of a first table storing the high and low level targeting on all age attributes, and a second table storing the high and low level for every age attribute.

The site preferably includes an arm, a body trunk and a leg.

The evaluating portion preferably calculates an age index indicating to which age attribute the calculated site ratio corresponds based on a distribution table representing a distribution of a site ratio for every age attribute, and the calculated site ratio as the site evaluation index.

(Deleted)

The body composition monitor preferably further includes a communication unit for transmitting information of the calculated site ratio to a server, wherein the communication unit receives information on a person with close balance of coverage of a body composition of the user from the server, and the output processing portion displays the information received by the communication unit on the display unit.

In accordance with another aspect of the present invention, the measurement result output method is a method for outputting a measurement result of a body composition executed in a computer including a storage unit and a display unit; the method including the steps of calculating a site ratio representing a ratio of a body composition value by site stored in the storage unit with respect to a body composition value of a whole body stored in the storage unit; calculating a site evaluation index representing an evaluation index related to the calculated site ratio; and displaying information including the site evaluation index on the display unit. The site evaluation index includes a high and low level representing a height of the site ratio.

The displaying step includes displaying a human body mark schematically showing a human body and also displaying a position in the human body mark corresponding to a site where the calculated high and low level is higher than average or a site where the calculated high and low level is lower than average of the site so as to be identifiable from other positions.

In accordance with still another aspect of the present invention, a measurement result output program product is a program for causing a computer to execute a method for outputting a measurement result of a body composition. The method includes the steps of calculating a site ratio representing a ratio of a body composition value by site with respect to a body composition value of a whole body; calculating a site evaluation index representing an evaluation index related to the calculated site ratio; and displaying information including the site evaluation index. The site evaluation index includes a high and low level representing a height of the site ratio.

The displaying step includes displaying a human body mark schematically showing a human body and also displaying a position in the human body mark corresponding to a site where the calculated high and low level is higher than average or a site where the calculated high and low level is lower than average of the site so as to be identifiable from other positions.

Effect of the Invention

According to the present invention, the ratio of the body composition value by site with respect to the body composition value of the whole body is calculated, and the evaluation index related to the calculated value is outputted. Therefore, a user can grasp whether there is bias in the coverage of body composition for every site.

MODE FOR CARRYING OUT THE INVENTION

Figure 1:
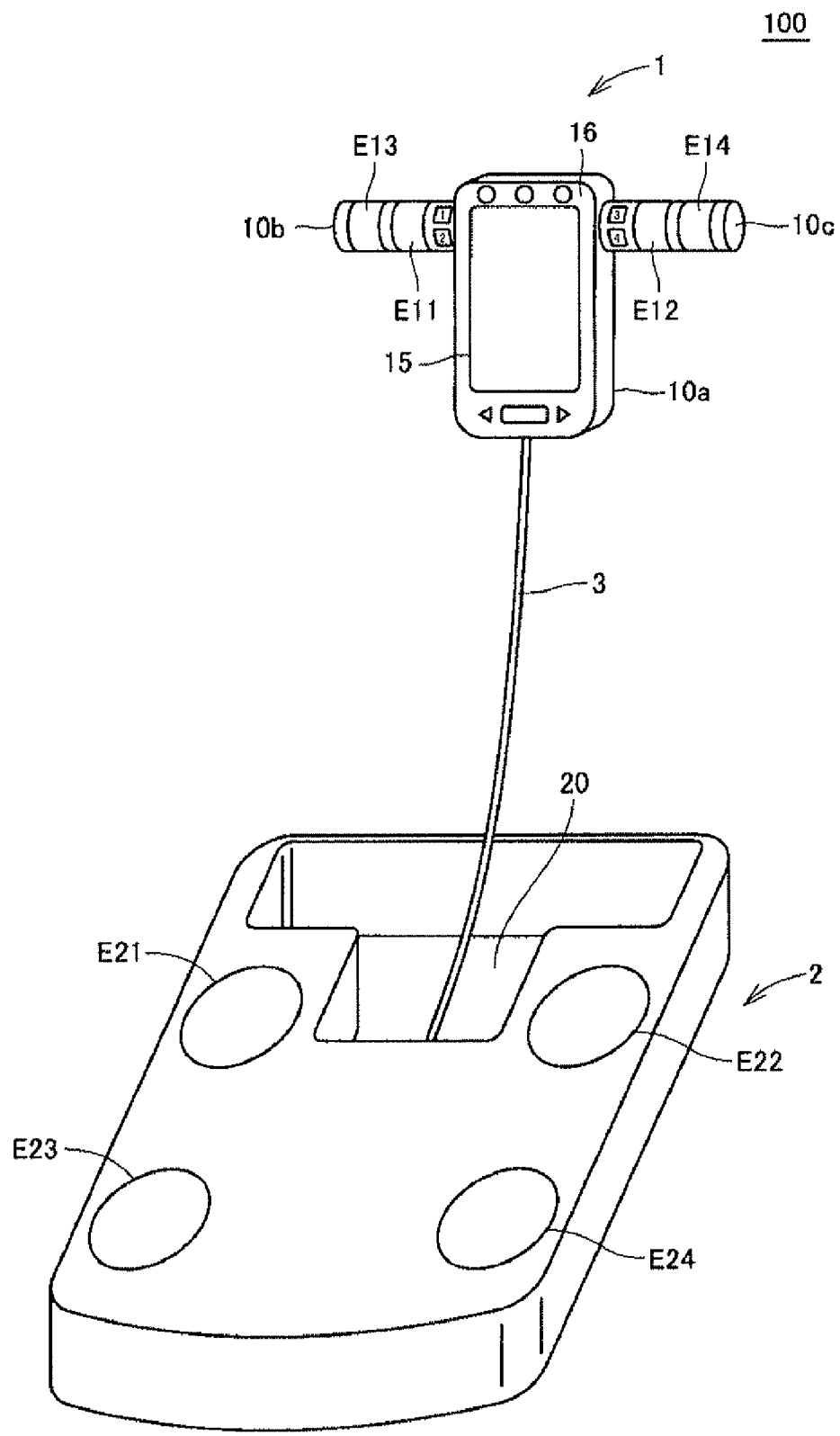
FIG. 1 is a view showing one example of an outer appearance of a body composition monitor according to an embodiment of the present invention.

Embodiments of the present invention will be described in detail with reference to the drawings. The same reference numerals are denoted for the same or corresponding portions in the figures, and the description thereof will not be repeated.

<Regarding Outer Appearance and Configuration>

(Outer Appearance Example)

FIG. 1 is a view showing one example of an outer appearance of a body composition monitor 100 according to an embodiment of the present invention.

With reference to FIG. 1, the body composition monitor 100 includes an upper limb unit 1 that can be gripped by a user with both hands, a lower limb unit 2 on which the user can place both feet, and a cable 3 for electrically connecting the upper limb unit 1 and the lower limb unit 2.

The upper limb unit 1 includes a main body 10a, and grips 10b, 10c respectively arranged on the left and the right of the main body 10a. The main body 10a includes a display unit 15 for displaying measurement results and various types of information, and an operation unit 16, which is operated by the user, for receiving instructions from the user and input of various types of information. The grips 10b, 10c include a plurality of electrodes E11, E12, E13, E14. The grips 10b, 10c are configured so as to be gripped by the user with both hands.

The grip 10b for the left hand includes the electrodes E11, E13, and the grip 10c for the right hand includes the electrodes E12, E14. The grip 10b for the left hand includes an electrode E11 for current application on the thumb side of the left hand, and includes an electrode E13 for voltage measurement on the little finger side of the left hand. Similarly, the grip 10c for the right hand includes an electrode E12 for current application on the thumb side of the right hand, and includes an electrode E14 for voltage measurement on the little finger side of the right hand.

Here, the upper limb unit 1 is described to include the grips 10b, 10c configured formed into a handle shape, but the upper limb unit 1 is not limited to such a mode. The upper limit unit 1 merely needs to be able to be gripped by the user with both hands, and the electrodes E11 to E14 are to be arranged at the portion to be gripped with both hands. That is, the electrodes E11, E13 are to be brought into contact with the left hand of the user, and the electrodes E12, E14 are to be brought into contact with the right hand.

A plurality of electrodes E21, E22, E23, E24 are arranged on the upper surface of the lower limb unit 2 (surface on which the user places both feet). Among such electrodes, the electrodes E21, E22 respectively arranged on the front side of the lower limb unit 2 (toe side of the user in the measurement position) are current application electrodes, and the electrodes E23, E24 respectively arranged on the back side of the lower limb unit 2 (heel side of the user in the measurement position) are voltage detection electrodes. The lower limb unit 2 includes an accommodating section 20 for accommodating the upper limb unit 1.

In the following description, the electrodes E11 to E14 are collectively referred to as "hand electrode E10", and the electrodes E21 to E24 are collectively referred to as "foot electrode E20".

(Hardware Configuration)

Figure 2:
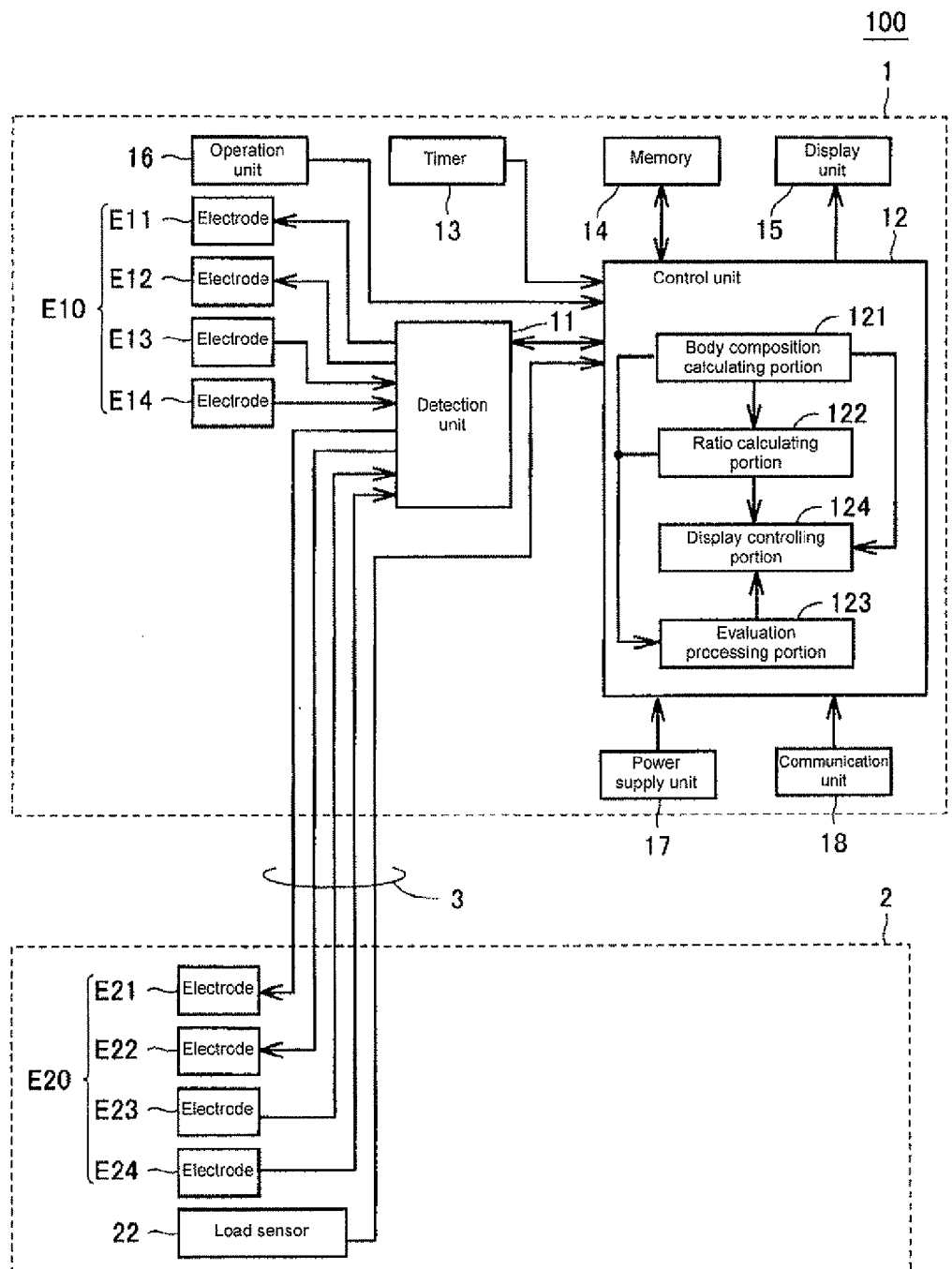
FIG. 2 is a block diagram showing a configuration example of the body composition monitor according to the embodiment of the present invention.

FIG. 2 is a block diagram showing a configuration example of the body composition monitor 100 according to the embodiment of the present invention.

In addition to the hand electrode E10, the display unit 15, and the operation unit 16, the upper limb unit 1 further includes a detection unit 11 for detecting a potential difference between at least the hand and the foot (whole body) by applying current between the hand and the foot of the user by both the hand electrode E10 and the foot electrode E20, a control unit 12 for controlling the entire body composition monitor 100, a timer 13 for measuring date and time, a memory 14 for storing various types of data and programs, a power supply unit 17 for supplying power to the control unit 12, and a communication unit 18 for performing transmission and reception of data and programs with an external terminal (not shown) such as a personal computer.

The lower limb unit 2 further desirably includes a load sensor 22 for measuring the weight of the user in addition to the foot electrode E20.

The memory 14 is configured by a nonvolatile memory such as a flash memory, for example. The structure example of the memory 14 will be specifically described later.

The display unit 15 is configured by an LCD (Liquid Crystal Display), for example.

The operation unit 16 includes a plurality of buttons, for example.

Figure 3:
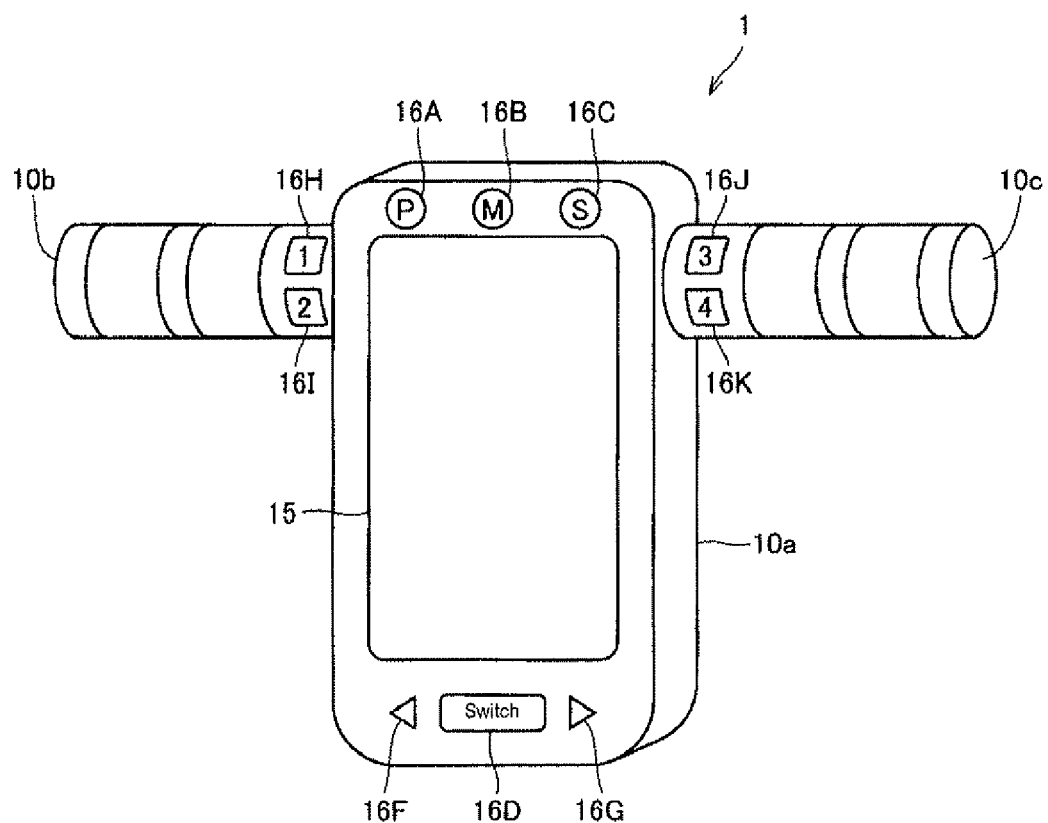
FIG. 3 is a view showing a specific example of a plurality of buttons arranged in an operation unit of the body composition monitor according to the embodiment of the present invention.

FIG. 3 is a view showing a specific example of the plurality of buttons arranged in the operation unit 16. With reference to FIG. 3, the operation unit 16 includes a power supply button 16A for instructing ON/OFF of the power supply, a memory button 16B for instructing display of the past measurement information, a measurement button 16C for instructing start of measurement, a display switch button 16D for instructing switching of the information being displayed on the display unit 15 to another information, and left and right buttons 16F, 160 for moving the cursor (not shown) displayed on the display unit 15 to the left and the right. The operation unit 16 may include a plurality of or four personal number buttons 16H 16I, 16J, 16K so that a plurality of users can use the body composition monitor 100. In the present embodiment, the operation unit 16 is assumed to include such personal number buttons 16H, 16I, 16J, 16K.

The detection unit 11 is controlled by the control unit 12 to switch the electrodes. The detection unit 11 further preferably detects the potential difference between the hands or between the feet by applying current between the hands or between the feet of the user by one of the hand electrode E10 and the foot electrode E20. The information of the detected potential difference is outputted to the control unit 12. The detection unit 11 is connected to all the hand electrodes E10 and the foot electrodes E20, for example, includes a changeover switch (not shown) for switching the electrodes according to the instruction from the control unit 12 and a constant current generating portion (not shown) for flowing a constant current to at least a pair of current electrodes selected by the changeover switch, and detects the potential difference of at least a pair of voltage electrodes selected by the changeover switch while constant current is applied to the user through the current electrode.

The control unit 12 is configured by a CPU (Central Processing Unit), for example.

(Function Configuration)

FIG. 2 shows the function configuration of the control unit 12. The control unit 12 includes a body composition calculating portion 121, a ratio calculating portion 122, an evaluation processing portion 123, and a display controlling portion 124 as the functions thereof.

The body composition calculating portion 121 calculates the body composition of the whole body or by site of the user. Here, the "body composition" refers to the proportion or the mass of the component composing the body (tissue constituting the body). In the present embodiment, in particular, the body composition includes an index that can be measured for both the whole body and by site, that is, at least any of a body fat percentage, a muscle percentage, a fat free mass, a body fat mass, and a muscle mass.

The body composition calculating portion 121 is described below as calculating the body fat percentage and the muscle percentage as the body composition.

The body composition calculating portion 121 first measures a whole body impedance, an inter-hand impedance, and an inter-feet impedance based on the potential difference between the hand and the foot, between the hands, and between the feet detected by the detection unit 11. The body composition of the whole body and by site of the user based on such measured impedances.

Each impedance is specifically measured in the following manner. When measuring the whole body impedance, the body composition calculating portion 121 flows current from the electrodes E11, E12 to the electrodes E21, E22, and performs control of detecting the potential difference between the electrodes E13, E14 and the electrodes E23, E24 while current is applied to the whole body of a subject. The whole body impedance is calculated (measured) based on the whole body potential difference detected in such a manner. When measuring the whole body impedance, the electrode E11 and the electrode E12, the electrode E21 and the electrode E22, the electrode E13 and the electrode E14, and the electrode E23 and the electrode E24 are preferably short circuited, respectively. When measuring the inter-hand impedance, the body composition calculating portion 121 flows current between the electrode E11 and the electrode E12, and performs control of detecting the potential difference between the electrode E13 and the electrode E14 while current is applied between the hands of the subject. When measuring the inter-foot impedance, the body composition calculating portion 121 flows current between the electrode E21 and the electrode E22, and performs control of detecting the potential difference between the electrode E23 and the electrode E24 while current is applied between the feet of the subject.

In the present embodiment, the body composition calculating portion 121 calculates the body fat percentage for the whole body and by site (e.g., arm, body trunk, leg) and the muscle percentage for the whole body and by site based on the whole body impedance, the inter-hand impedance, and the inter-foot impedance.

The calculation formula of the body fat percentage (% FAT) of the whole body is expressed with the following equations (1), (2).

$$\% \text{ FAT}=(W-FFM)/W \cdot 100 \qquad (1)$$

$$FFM=a \cdot H^2/Zw+b \cdot W+c \cdot Ag+d \qquad (2)$$

(where, FFM: fat free mass, W: weight, H: height, Zw: whole body impedance, Ag: age, a to d: constant)

The constants a to d are defined in advance by correlation with the reference measured with DEXA (Dual Energy X-ray Absorptiometry) and the like. The constants a to d may differ by sex.

The body fat percentage by site is calculated based on the correlation with the reference measured with the DEXA and the like in advance from the measured inter-hand impedance and the inter-foot impedance, and the physical information of the user, for example.

The muscle percentage of the whole body and by site is also calculated by a known method, similar to the case of the body fat percentage.

The ratio calculating portion 122 calculates the ratio of the body composition value by site with respect to the body composition value of the whole body, that is, the site ratio based on the calculation result by the body composition calculating portion 121. The site ratio for the body fat percentage is obtained by dividing the body fat percentage by site with the body fat percentage of the whole body. The site ratio for the muscle percentage is obtained by dividing the muscle percentage by site with the muscle percentage of the whole body.

The evaluation processing portion 123 calculates an evaluation index (hereinafter referred to as "whole body evaluation index") of the body composition of the whole body of the user based on the physical attribute of the user and the body composition value of the whole body. In the present embodiment, the "physical attribute" includes at least sex, and may include an age index in addition to the sex. Furthermore, the "age index" represents one of the age and the age attribute.

A plurality of levels such as whether the body composition value of the whole body of the user is low (small), high (large), or standard compared to the standard value in the physical attribute of the user is used for the whole body evaluation index. In the present embodiment, the calculation (determination) of such high and low levels is carried out using a whole body evaluation table 1401 (FIG. 4), to be described later. The evaluation determination by such levels can be realized by a method carried out from the conventional art. Therefore, the details on the calculation of the whole body evaluation index (high and low level) will not be described.

The evaluation processing portion 123 further calculates the evaluation regarding the site ratio (hereinafter referred to as "site evaluation index") based on the physical attribute of the user and the site ratio.

In the present embodiment, the evaluation processing portion 123 performs determination by a plurality of levels for the site evaluation index, similar to the whole body evaluation index. That is, determination on whether or not the site ratio of the user is low (small), high (large), or standard compared to the standard value in the physical attribute of the user is performed. The evaluation processing portion 123 calculates the high and low level of the site ratio using a site evaluation table 1402 (FIG. 4), to be described later.

The evaluation processing portion 123 also calculates, as the site evaluation index, the age index indicating to the standard value of which age attribute the site ratio of the user corresponds. The site ratio is the ratio of the body composition value by site with respect to the body composition value of the whole body, and represents the balance in covering of the fat and the muscle, and thus the age index is referred to as "balance age" in the present embodiment. A distribution table 1403 (FIG. 4), to be described later, is used for the calculation of the balance age.

The specific calculation method for the high and low level and the balance age with respect to the site ratio will be described in detail later.

Only one of the high and low level and the balance age may be calculated.

The display controlling portion 124 may perform control to display the site ratio calculated by the ratio calculating portion 122 and the site evaluation index (high and low level, balance age) with respect to the site ratio calculated by the evaluation processing portion 123 on the display unit 15. Only one of the site ratio and the site evaluation index may be displayed.

The display controlling portion 124 may display the body composition value of the whole body calculated by the body composition calculating portion 121 and the whole body evaluation index (high and low level) calculated by the evaluation processing portion 123 on the display unit 15. In this case as well, only one of the body composition value of the whole body and the whole body evaluation index may be displayed.

In the present embodiment, information regarding the site ratio and the like are outputted by display, but the present invention is not limited to such an example. For example, such information may be outputted by a printing process by a printer (not shown). Alternatively, such information may be outputted (recorded) in a removable recording medium (not shown) or may be outputted (transmitted) to an external terminal (not shown) through the communication unit 18.

The operations of the function blocks may be realized by executing software stored in the memory 14, or at least one operation may be realized by hardware.

(Structure Example of Memory)

A structure example of the memory 14 will now be described in detail.

Figure 4:
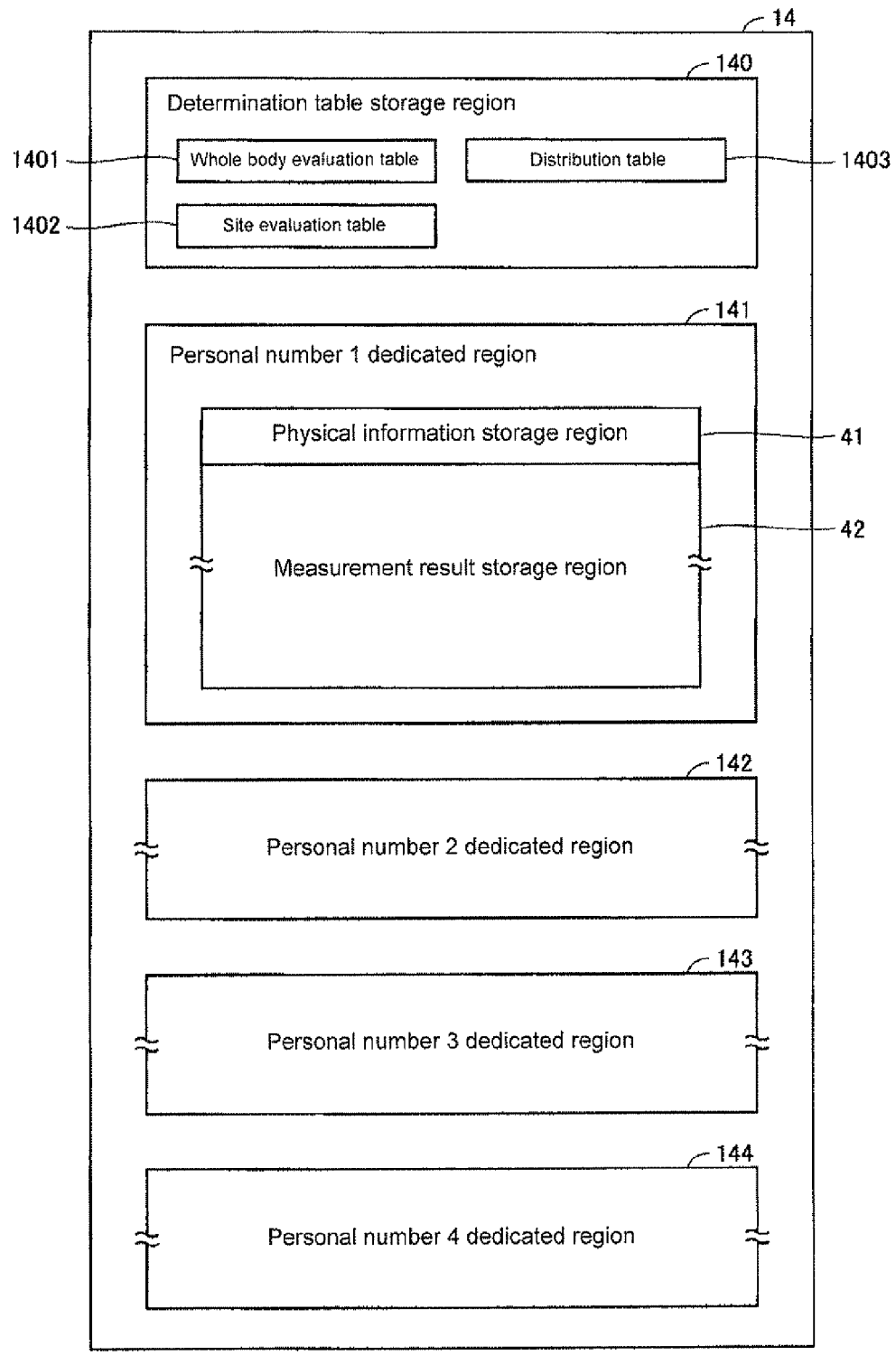
FIG. 4 is a view showing a structure example of a memory of the body composition monitor according to the embodiment of the present invention.

FIG. 4 is a view showing a structure example of the memory 14. With reference to FIG. 4, the memory 14 includes a table storage region 140, a region 141 for storing information related to the user corresponding to personal number 1, a region 142 for storing information related to the user corresponding to personal number 2, a region 143 for storing information related to the user corresponding to personal number 3, and a region 144 for storing information related to the user corresponding to personal number 4.

The region 141 includes a physical information storage region 41 for storing the physical information of the user corresponding to the personal number 1 and a measurement result storage region 42 for storing the measurement result of the user corresponding to the personal number 1. The regions 142 to 144 corresponding to other personal numbers are assumed to include storage regions similar to the region 141.

The "physical information" is the information necessary for calculating the body composition and includes age, sex, height, and weight. The body composition monitor 100 according to the present embodiment includes the load sensor 22, so that the age data, the sex data, and the height data based on the input from the user of the physical information are stored in the physical information storage region 41.

Figure 5:
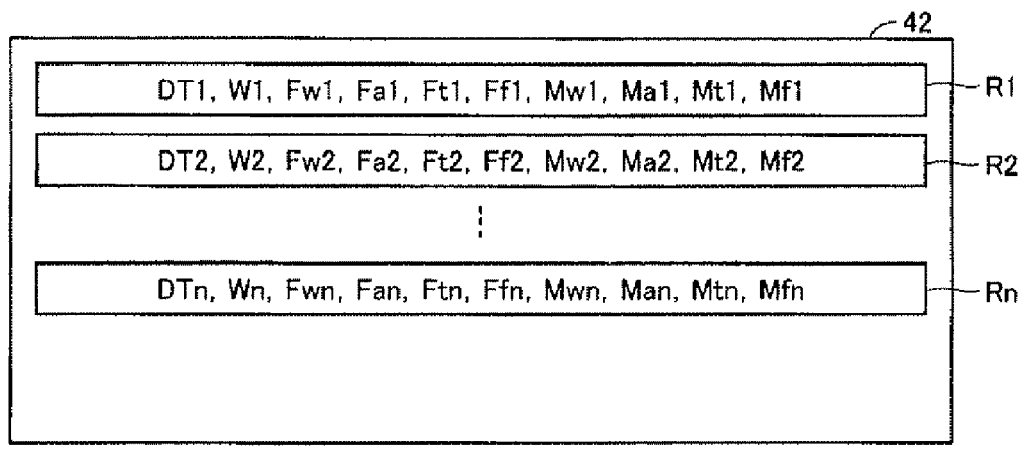
FIG. 5 is a view showing one example of a data structure of a measurement result storage region according to the embodiment of the present invention.

One example of the data structure of the measurement result storage region 42 is shown in FIG. 5. When the body composition measurement process, to be described later, is executed, the measurement result is stored in units of records R in the measurement result storage region 42 corresponding to the personal number specified by the user. The record R (R1, R2, ..., Rn) includes date and time data DT of the body composition measurement (e.g., potential difference detection), weight value data W as physical information, body fat percentage data Fw of the whole body, body fat percentage data Fa of the arm, body fat percentage data Ft of the body trunk, body fat percentage Ff of the leg, muscle percentage data Mw of the whole body, muscle percentage data Ma of the arm, muscle percentage data Mt of the body trunk, and muscle percentage Mf of the leg. Such data merely need to be stored in each region in correspondence with each measurement, and is not limited to the storage form using the record R.

In the present embodiment, each storage region is provided in advance for each personal number. However, the information of the physical information, the measurement result, and the reference value of the user merely need to be stored in association with the personal number, and the storage region for each personal number may not be provided.

The table storage region 140 includes the whole body evaluation table 1401, the site evaluation table 1402, and the distribution table 1403.

The whole body evaluation table 1401 is used to calculate (determine) the whole body evaluation index described above. The whole body evaluation table 1401 has the range of body composition value defined in correspondence with four levels of large, slightly large, normal, and small for each sex with respect to each body composition.

The site evaluation table 1402 has the relationship of the high and low level of the site ratio and the site ratio defined for every physical attribute, and is used to calculate (determine) the high and low level, which is one type of site evaluation index. The site evaluation table 1402 may store the high and low level targeting on all age attributes, or may store the high and low level for every age attribute. That is, the physical attribute used in defining the high and low level may be only sex, or may be sex and age attribute (generation). In the present embodiment, the latter is adopted. Both types of tables are stored, and both the high and low level targeting on all age attributes and the high and low level corresponding to the age attribute of the user may be calculated.

Figure 6:
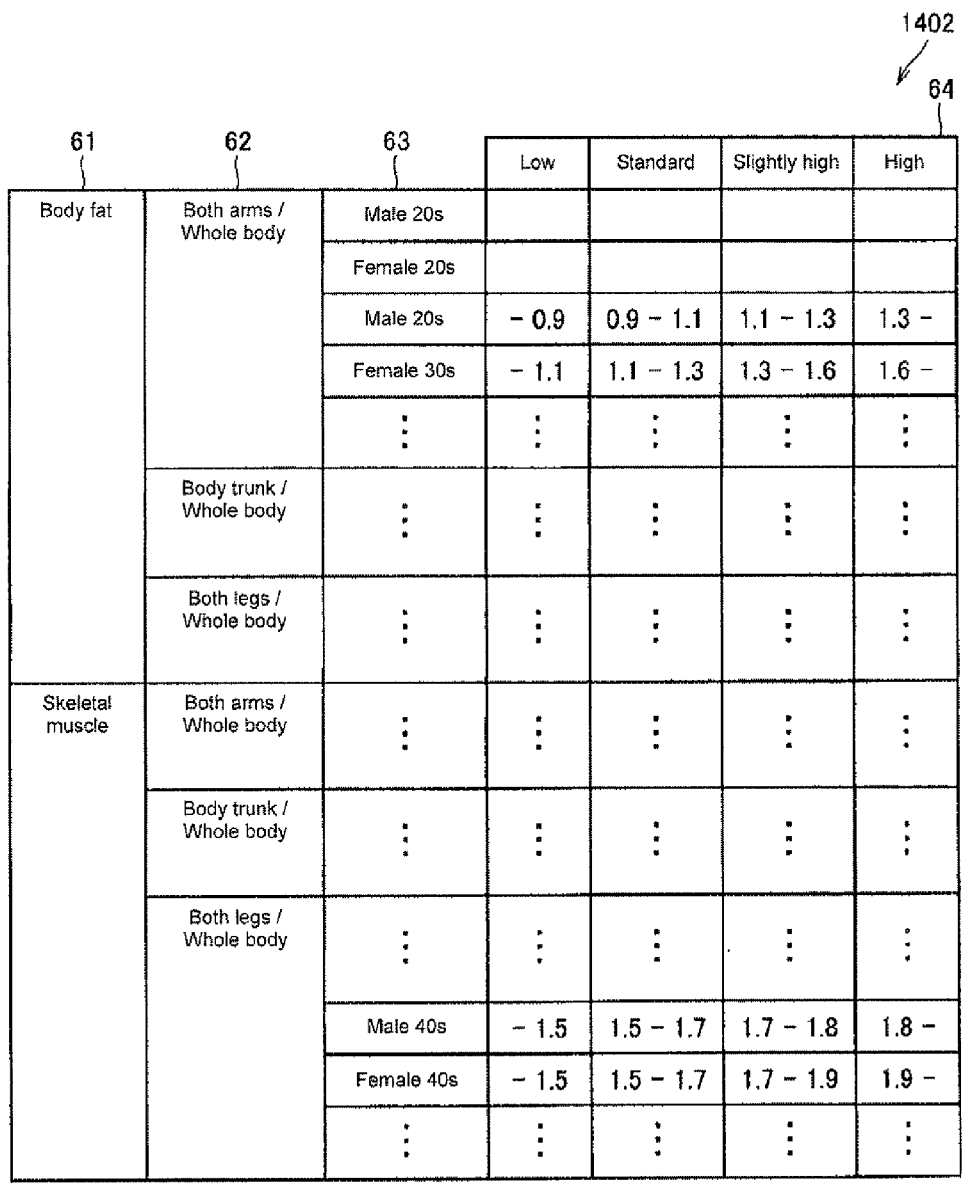
FIG. 6 is a view showing a data structure example of a table (site evaluation table) used in the evaluation of a site ratio in the embodiment of the present invention.

FIG. 6 is a view showing a data structure example of the site evaluation table 1402. With reference to FIG. 6, the site evaluation table 1402 includes an item 61 showing the body composition, an item 62 showing the site, an item 63 showing the physical attribute, and an item 64 showing the high and low level.

In the column of the item 61, the body fat percentage and the muscle percentage are stored as information indicating the type of body composition.

In the column of the item 62, the arm (both arms/whole body), body trunk (body trunk/whole body) and leg (both legs/whole body) are stored as Information for specifying the site to be divided by the body composition value of the whole body. Such information is made in correspondence with every type of body composition.

In the column of the item 63, male 20s, female 20s, male 30s, female 30s, and the like are stored as information for specifying the physical attribute. Such information is stored for every site to be divided by the body composition value of the whole body.

In the row of the item 64, four levels, that is, low, standard, slightly high, and high are stored. In the column of the item 64, data indicating the range of the corresponding body composition value is stored for every level. The data indicating the range of the corresponding body composition value is stored for every physical attribute.

The range of the body composition value for every physical attribute corresponding to each level is assumed to be defined based on the result of clinical experiment and the like conducted in advance.

The distribution table 1403 stores data indicating the distribution of the site ratio for every generation (age attribute). For example, the ratio "body trunk/whole body" of the body fat percentage has a distribution shown in FIG. 7 for every generation.

Figure 7:
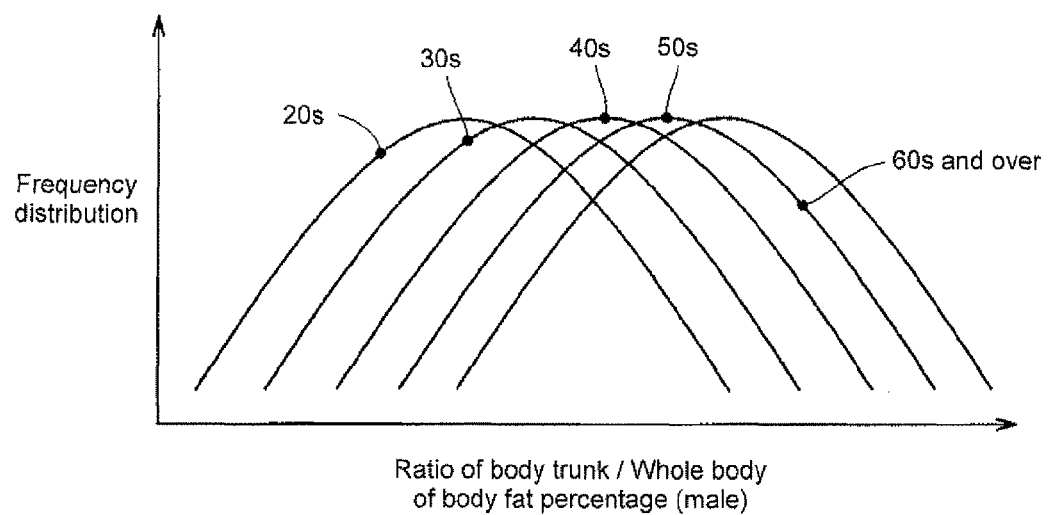
FIG. 7 is a view showing a data structure example of a distribution table used in the calculation of an age index in the embodiment of the present invention.

FIG. 7 is a graph showing the frequency distribution by generation having the frequency distribution on the vertical axis and the "ratio of body trunk/whole body of body fat percentage" on the horizontal axis. The graph of FIG. 7 is assumed to be a frequency distribution targeting on male.

The body fat percentage of the body trunk generally tends to become higher compared to the body fat percentage of the whole body with aging. Therefore, the ratio of the body trunk/whole body of the body fat percentage becomes greater with aging, as shown in FIG. 7.

The information of the frequency distribution for every generation is also stored for the ratio of other sites, that is, the ratio of arm/whole body and the ratio of leg/whole body. The frequency distribution for every generation is assumed to be based on the result of clinical experiment and the like conducted in advance.

In the present embodiment, various types of evaluation processes are carried out using the tables 1401 to 1403 described above, but the present invention is not limited thereto, and various types of evaluation processes may be carried out using a predetermined calculation formula.

<Regarding Operation>

Figure 8:
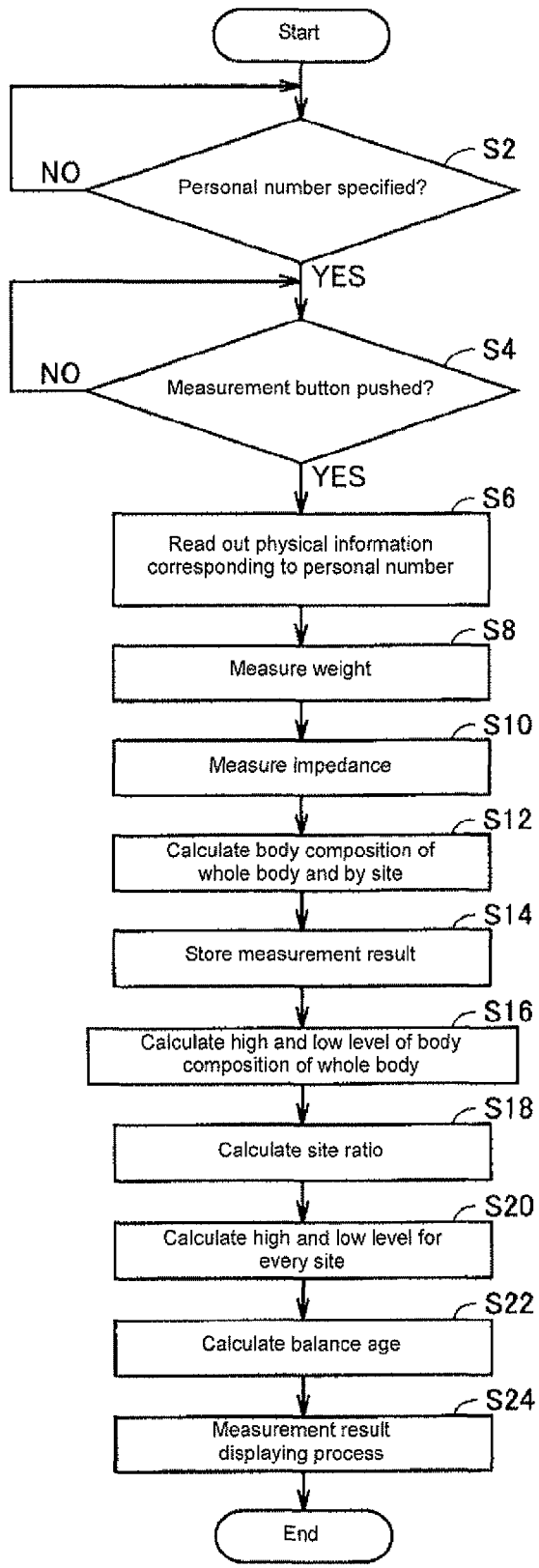
FIG. 8 is a flowchart showing a body composition measurement process executed by the control unit of the body composition monitor in the embodiment of the present invention.

FIG. 8 is a flowchart showing a body composition measurement process executed by the control unit 12 of the body composition monitor 100 according to the embodiment of the present invention. The processes shown in the flowchart of FIG. 8 are stored in the memory 14 as a program in advance, and the control unit 12 reads out and executes this program to realize the function of the body composition measurement process.

With reference to FIG. 8, the control unit 12 first determines whether or not a personal number is specified by a user (step S2). In other words, it is determined whether or not one of the buttons 16H to 16K is pushed by the user. The control unit 12 waits until the personal number is specified (NO in step S2). If determined that the personal number is specified (YES in step S2), the process proceeds to step S4.

In step S4, the control unit 12 determines whether or not the measurement button 16C is pushed. The control unit 12 waits until the measurement button 16C is pushed (NO in step S4). When the measurement button 16C is pushed (YES in step S4), the process proceeds to step S6.

In step S6, the body composition calculating portion 121 reads out the physical information (height, age, sex) corresponding to the personal number specified by the user. For example, assume that the personal number switch 16H corresponding to the personal number 1 is pushed in step S2. In this case, the height data, the age data, and the sex data are read out from the physical information storage region 41 in step S6. The read physical information is temporarily recorded in the internal memory.

Next, the body composition calculating portion 121 measures the weight based on a signal from the load sensor 22 (step S8). The measured weight value is temporarily recorded in the internal memory.

Thereafter, the body composition calculating portion 121 executes the impedance measurement process (step S10). Specifically, the detection unit 11 is controlled to measure the whole body impedance, the inter-hand impedance, and the inter-leg impedance. The value of each measured impedance is temporarily recorded in the internal memory.

The body composition calculating portion 121 calculates the body composition of the user based on each data temporarily recorded in the internal memory, a predetermined calculation formula as described above, and the like (step S12). Specifically, the body fat percentage of each of the whole body, the arm, the body trunk, and the leg of the user, and the muscle percentage of each of the whole body, the arm, the body trunk, and the leg are calculated. The control unit 12 then stores the value of the body composition of this time calculated in step S12 in the measurement result storage region 42 (step S14).

The evaluation processing portion 123 then calculates a general evaluation for each body composition of the whole body (step S16). That is, the high and low level of the body fat percentage of the whole body and the high and low level of the muscle percentage of the whole body are determined using the whole body evaluation table 1401.

The ratio of "site/whole body", that is, the site ratio (ratio of site body composition value with respect to body composition value of whole body) is also calculated for each body composition (step S18). Specifically, the ratio of the arm/whole body, the ratio of the body trunk/whole body, and the ratio of the leg/whole body are calculated for the body fat percentage and for the muscle percentage.

The evaluation processing portion 123 calculates the high and low level for every site (step S20). Specifically, the high and low level for six types of site ratios calculated in step S18 is calculated. More specifically, the site evaluation table 1402 is searched, and the level corresponding to each site ratio of the user of the four stored levels is extracted. In the present embodiment, the high and low level of the ratio of the arm/whole body, the high and low level of the ratio of the body trunk/whole body, and the high and low level of the ratio of the leg/whole body are extracted for the body fat percentage and for the muscle percentage.

The evaluation processing portion 123 further calculates a balance age for the site ratio of the body fat percentage and the muscle percentage (step S22). Specifically, the balance age of the user is calculated based on the distribution information for every generation stored in the distribution table 1403. One example of a method for calculating the balance age according to the present embodiment is shown in FIG. 9.

Figure 9:
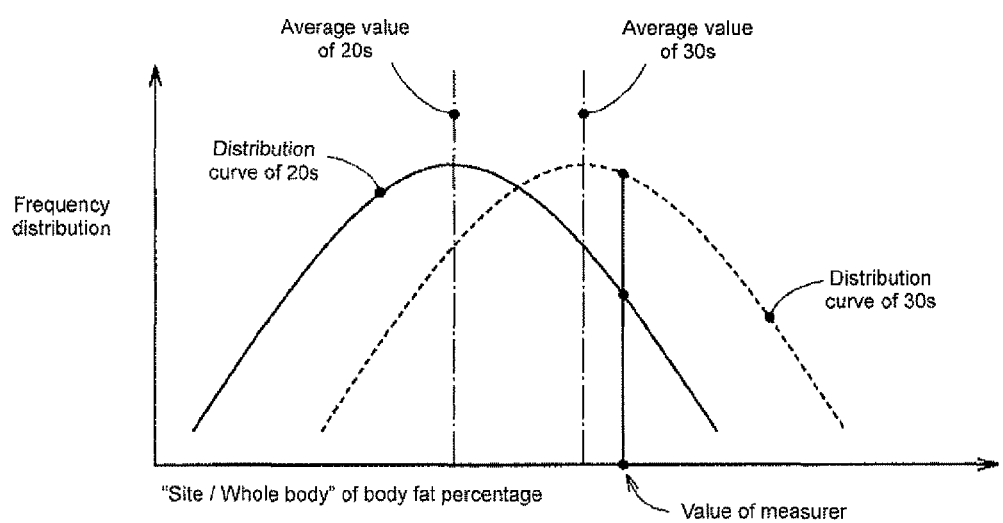
FIG. 9 is a view describing one example of a method for calculating a balance age.

With reference to FIG. 9, assume that the user is in the 20s, for example. The value (e.g., body trunk/whole body) for the body fat percentage of the user (measurer) is assumed to exceed the average of the 30s (smaller than average of 40s). In this case, the evaluation processing portion 123 determines that the body fat percentage of the body trunk of the user corresponds to 30s, and determines the balance age of the body fat percentage of the body trunk as 30s. It should be noted that the present invention is not limited to such a method, and the balance age may be determined as 30s when the site ratio of the body fat percentage of the user (measurer) is closer to the average of the 30s than the average of the 20s.

After the balance age of each site is calculated for the body fat percentage according to such a method, the evaluation processing portion 123 calculates the average value of the generation for every site with respect to the body fat percentage. The calculated average value is determined as the "average balance age" of the site ratio of the user for the body fat percentage.

The method for calculating each balance age and the average balance age for the muscle percentage is similar to that for the body fat percentage, and thus the description thereof will not be repeated.

When using only the average value (standard value) of each generation in the calculation of the balance age, the data in the site evaluation table 1402 may be used. That is, in the site evaluation table 1402, the average value of the site ratio which level of the item 64 is "standard" may be the average value of each generation. In this case, the distribution table 1403 may not be stored in the memory 14.

The display controlling portion 124 performs the measurement result displaying process according to the calculation results of steps S12, S16, S18, S20, S22 (step S24). The details on the measurement result displaying process will be described later.

The body composition measurement process according to the present embodiment is then terminated.

(Regarding Measurement Result Displaying Process)

In the present embodiment, for example, the measurement result for the body fat percentage is first displayed, and thereafter, the measurement result for the muscle percentage is displayed if the display switch button 16D is pushed by the user. The type of body composition to be displayed first may be selected by the user. In this case, information for identifying whether the type of body composition to be displayed first is the body fat percentage or the muscle percentage is to be stored in the memory 14.

Figure 10:
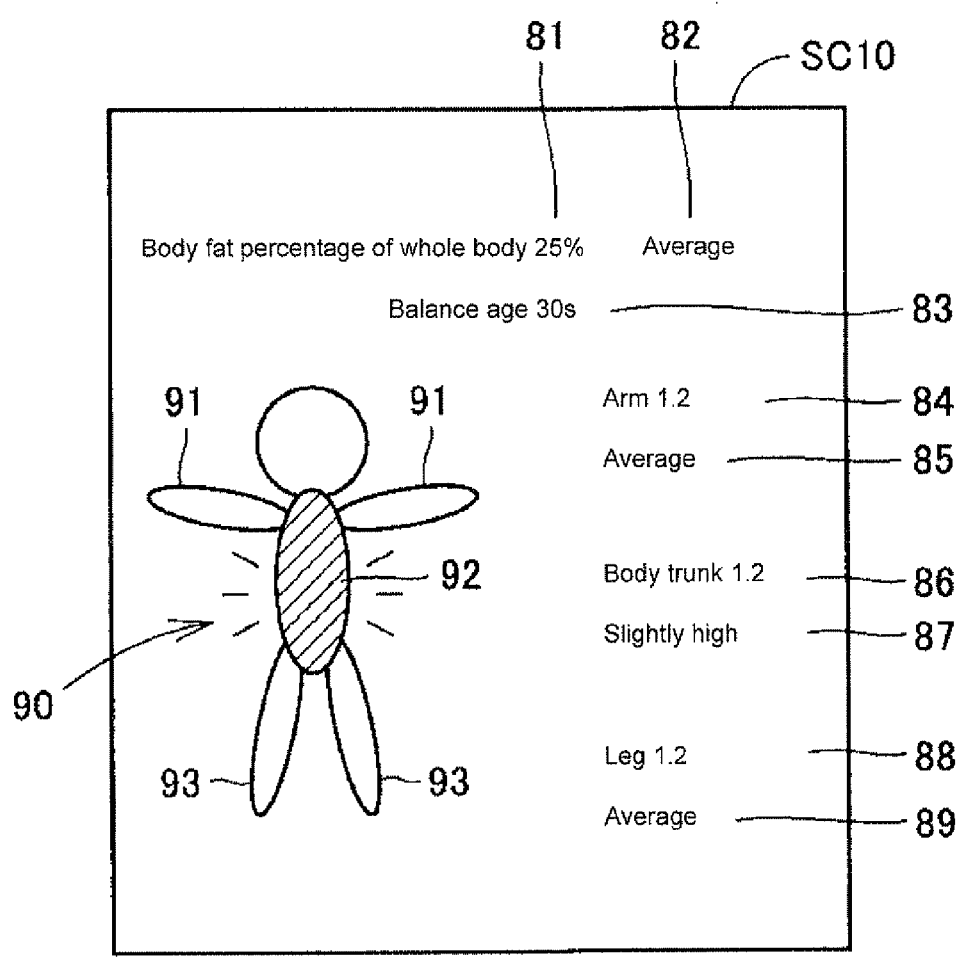
FIG. 10 is a view showing one example of a screen displayed as a measurement result of the body fat percentage in the embodiment of the present invention.

FIG. 10 is a view showing one example of a screen displayed as a measurement result of the body fat percentage in the embodiment of the present invention.

In step S24, a screen SC10 as shown in FIG. 10 is displayed on the display unit 15. In the screen SC10, a body fat percentage 81 of the whole body, a high and low level 82 of the body fat percentage of the whole body, and a balance age 83 of the user are displayed. The body fat percentage 81 of the whole body indicates the value calculated in step S12. The high and low level 82 of the body fat percentage of the whole body indicates the level calculated in step S16. The balance age 83 indicates the average balance age calculated in step S22.

In the screen SC10, the site ratio of the body fat percentage and the calculation result of the high and low level are also displayed for every site. Specifically, a site ratio 84 of the arm, a high and low level 85 of the arm, a site ratio 86 of the body trunk, a high and low level 87 of the body trunk, a site ratio 88 of the leg, and a high and low level 89 of the leg are displayed. The site ratio 84 of the arm, the site ratio 86 of the body trunk, and the site ratio 88 of the leg indicate the values calculated in step S18. The high and low level 85 of the arm, the high and low level 87 of the body trunk, and the high and low level 89 of the leg indicate the high and low level for every site calculated in step S20.

As the site ratio of the body fat percentage and the calculation result of the high and low level are displayed for every site, the user is able to recognize whether the occupying proportion of the body fat percentage of each site with respect to the body fat percentage of the whole body of himself/herself is high or low compared to other people having the same value of the physical attribute as that of the user. As a result, the user can specifically grasp the body fat percentage of which site should be reduced with effort.

The information (body fat percentage, high and low level) on the body fat percentage of the whole body are displayed in association with the high and low level for every site. Therefore, even if the body fat percentage of the whole body of the user is an average value in the physical attribute of the user, the degree of bias of the fat coverage for every site can be recognized so that a well-focused exercise can be carried out. Furthermore, even if the body fat percentage of the whole body of the user is higher than the standard value in the physical attribute of the user, the full body exercise needs to be carried out if the fat coverage for every site has no bias (balanced).

In the present embodiment, the high and low level of the ratio for every site is displayed with characters. However, the high and low level of the ratio for every site may be displayed with a bar of a plurality of stages (e.g., 12 stages) as in the conventional art.

In the screen SC10, a human body mark 90 schematically showing the human body is also displayed. The human body mark 90 includes an arm 91, a body trunk 92, and a leg 93. The displayed mark (figure) is not limited to the shape of the human body mark 90 as long as the arm, the body trunk, and the leg can be specified.

The display controlling portion 124 flashes and displays the site (position) which high and low level of the site ratio is higher than the average of the arm 91, the body trunk 92, and the arm 93 of the human body mark 90. The user (measurer) thus can intuitively grasp the ratio of the body fat percentage of which site is high in the physical attribute of the user.

In the present embodiment, the site which high and low level of the site ratio is higher than average is flashed, but the present invention is not limited to such a display form as long as the relevant site can be displayed in an identifiable manner from the other sites (site which high and low level is smaller than or equal to average).

Figure 11:
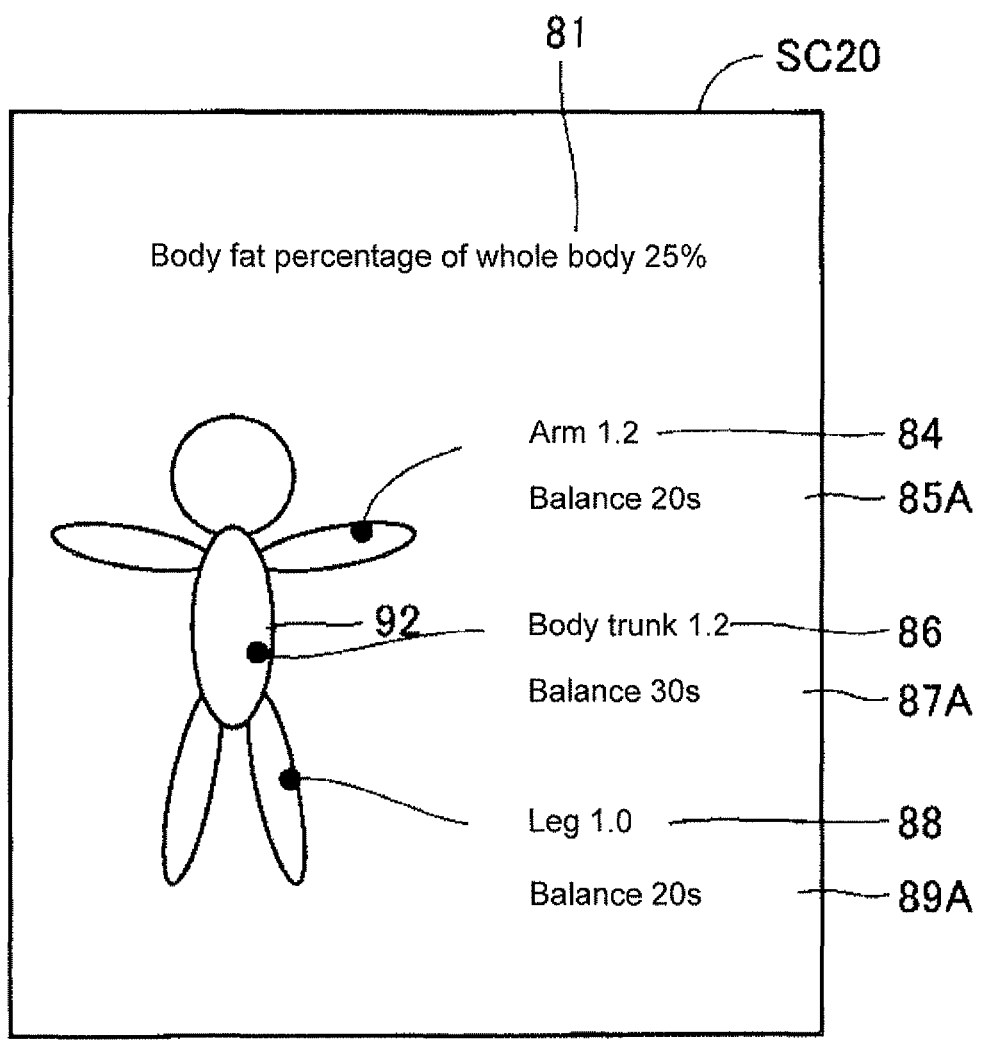
FIG. 11 is a view showing another example of a screen displayed as a measurement result of the body fat percentage in the embodiment of the present invention.

If the user pushes the display switch button 16D while the screen such as the screen SC10 is displayed, the display controlling portion 124 may display the balance age for every site such as a screen SC20 shown in FIG. 11.

With reference to FIG. 11, the balance ages (generation) 85A, 87A, 89A for every site are displayed on the screen SC20 instead of the high and low levels 85, 87, 89 for every site displayed on the screen SC10. In this case as well, the balance age for every site is displayed with characters, but may be displayed with a bar of a plurality of stages in units of generation.

In the screen SC20, the high and low level 82 of the body fat percentage of the whole body and the average balance age 83 in the screen SC10 are not displayed, but such information may also be displayed in the screen SC20.

In the present embodiment, both the ratio for every site and the site evaluation index (high and low level, balance age) are displayed in both screens SC10, SC20 as information related to the site ratio, but only one of the ratio for every site and the site evaluation index may be displayed.

Figure 12:
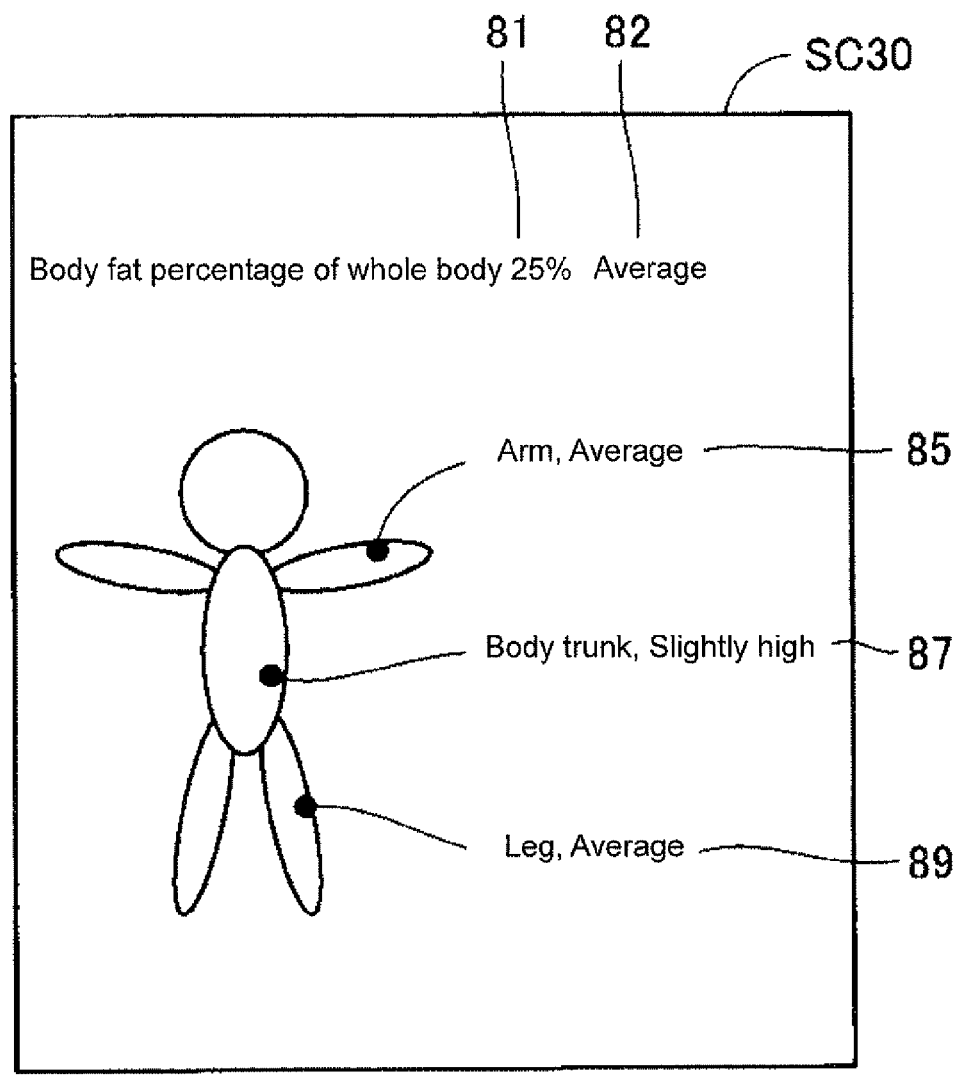
FIG. 12 is a view showing still another example of a screen displayed as a measurement result of the body fat percentage in the embodiment of the present invention.

A screen SC30 of FIG. 12 shows an example in which only the high and low levels 85, 87, 89 for every site are displayed as information related to the site ratio.

The display controlling portion 124 further displays the measurement result for the muscle percentage in response to the instruction of display switching from the user. The display similar to the body fat percentage is carried out for the muscle percentage. Therefore, the detailed description will not be repeated here. In the case of the muscle percentage, the site to be flashed in the human body mark 90 may be a site which high and low level of the site ratio is lower than average.

Alternatively, in the present embodiment, the high and low level to be displayed in flashing manner is assumed to be defined in advance according to the type of body composition, but the high and low level to be displayed in flashing manner may be selected (specified) by the user. In this case, the information of the high and low level to be displayed in flashing manner is to be stored in the memory 14 for every type of body composition.

Alternatively, a plurality of goals (e.g., diet, muscle building, and the like) may be presented to the user, and the level to be flashed may be changed according to the goal when one of the goals is selected. For example, if the goal is diet, the site which body fat percentage is higher than average may be displayed in flashing manner, and if the goal is muscle building, the site which body fat percentage is lower than average may be displayed in flashing manner. The presentation and selection of the target may be carried out independently from the body composition measurement process. If the goal is not selected, the level to be flashed may be changed according to the physical attribute (sex, age attribute) of the user.

As described above, according to the embodiment of the present invention, information related to the ratio of the body composition value by site with respect to the body composition value of the whole body is displayed (outputted). Therefore, the user can grasp the degree of bias of the fat and the muscle for every site. The user thus can carry out an appropriate exercise according to his/her goal (e.g., diet, muscle building).

In the present embodiment, the high and low level and the age index in the age attribute of the user are calculated, so that whether the balance of his/her fat and muscle coverage is low or high compared to the standard value of his/her generation can be easily grasped.

In the present embodiment, the measurement results of both the body fat percentage and the muscle percentage are displayed. However, the type of body composition to be displayed may be defined according to the goal or the physical attribute of the user. The display order may be determined according to the goal or the physical attribute of the user. For example, the display of the body fat percentage may be prioritized for female, and the display of the muscle percentage may be prioritized for elderly (e.g., over 50s). The display of the body fat percentage/muscle percentage for every site may be prioritized for the user whose goal is muscle building. The body fat percentage/muscle percentage for every site is obtained by dividing the site ratio of the body fat percentage by the site ratio of the muscle percentage for every site.

In the present embodiment, an example for the body fat percentage and the muscle percentage has been described, but the degree of bias of the fat and the muscle may be more directly determined or displayed by the body fat mass and the muscle mass.

<First Variant>

In the above embodiment, the user can recognize which site to tone up in a concentrated manner by displaying the information related to the site ratio.

In addition, if an instruction is made from the user, the information on to which person (celebrity) the balance of the fat or the muscle of every site of the user is close to can be further presented.

In this case, the communication unit 18 transmits the information of the site ratio calculated in step S18 of FIG. 8 and receives the information on the person having a close balance on the coverage of the body composition of the user by the server. The server holds in advance one or more human data in correspondence with the combination of the ratio of the arm, the body trunk, and the leg.

The display controlling portion 124 displays the received information of the human on the display unit 15.

Such process may be carried out after step S24 of FIG. 8.

<Second Variant>

In the above embodiment, all the body composition measurement processes shown in FIG. 8 are executed in the body composition monitor 100. However, the process related to the output (display) of the measurement result (e.g., processes of steps S16 to S24) of the processes shown in FIG. 8 may be executed in another computer. That is, the computer that executes the output process of the measurement result is not limited to the body composition monitor 100, and may be an information processing terminal such as a personal computer or a portable terminal.

Figure 13:
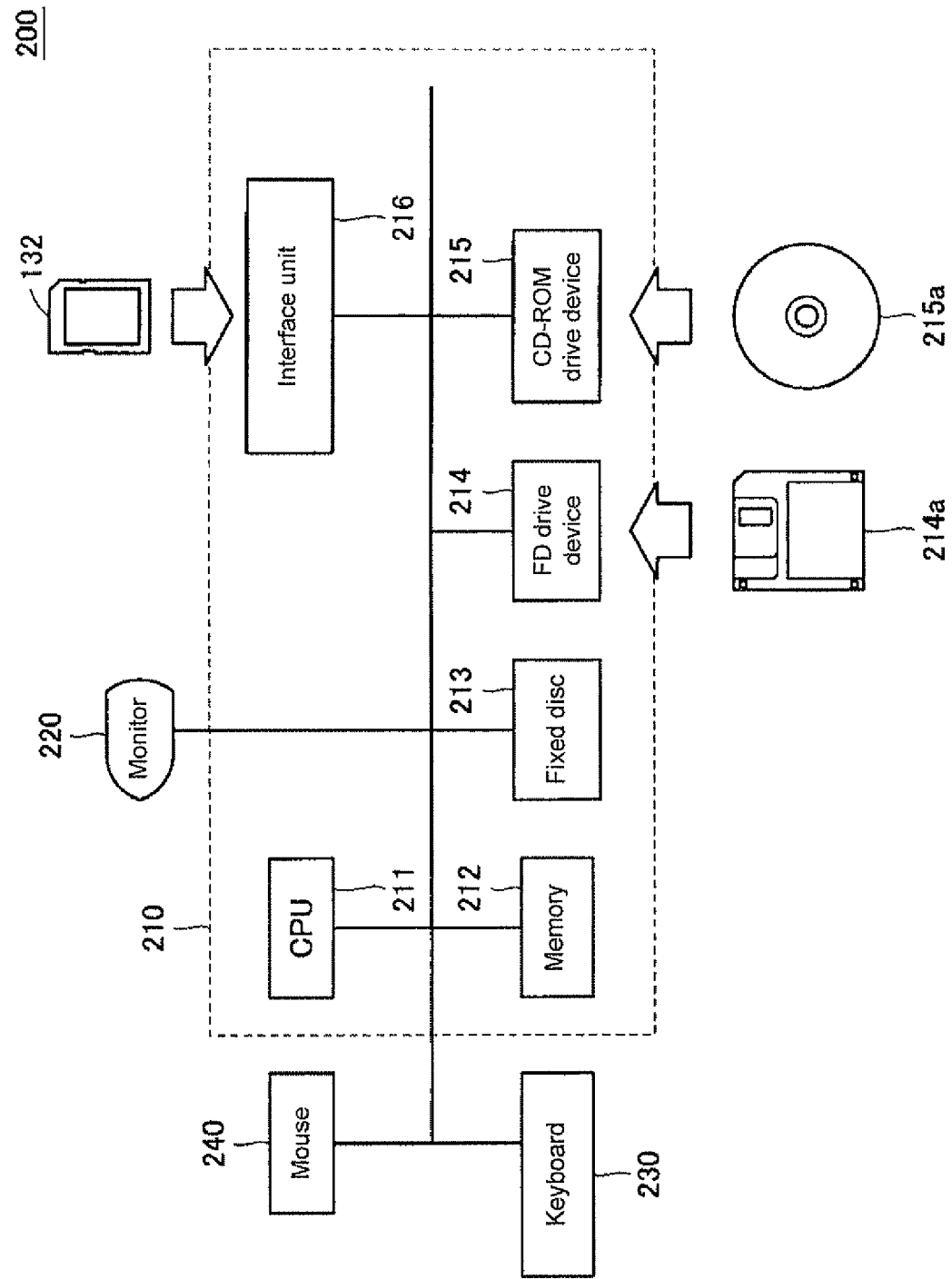
FIG. 13 is a block diagram showing one example of a hardware configuration of an information processing device capable of executing the measurement result output process in a second variant of the embodiment of the present invention.

FIG. 13 is a block diagram showing one example of a hardware configuration of an information processing device 200 capable of executing the measurement result output process in the second variant of the embodiment of the present invention.

With reference to FIG. 13, the information processing device 200 includes an information processing device main body 210, a monitor 220, a keyboard 230, and a mouse 240, and the information processing device main body 210 includes a CPU 211, a memory 212, a fixed disc 213 serving as a storage device, an FD (Flexible Disk) drive device 214, a CD-ROM (Compact Disk-Read Only Memory) drive device 215, and an interface unit 216. Such pieces of hardware are mutually connected with a bus.

An FD 214*a* is attached to the FD drive device 214, and a CD-ROM 215*a* is attached to the CD-ROM drive device 215. The information processing device 200 according to the present embodiment is realized when the CPU 211 executes a software using hardware such as the memory 212. Such software is generally stored in a computer readable non-transitory recording medium such as the FD 214*a* or the CD-ROM 215*a*, or is circulated through the network or the like. Such software is then read from the recording medium by the FD drive device 214 or the CD-ROM drive device 215, or received by a communication interface (not shown) and stored in the fixed disc 213. The software is further read from the fixed disc 213 to the memory 212 and executed by the CPU 211.

The monitor 220 is a display unit for displaying information such as the measurement result of the body composition outputted by the CPU 211, and is configured by an LCD, a CRT (Cathode Ray Tube), or the like by way of example. The mouse 240 accepts the command from the user corresponding to the operation such as click or slide. The keyboard 230 accepts the command from the user corresponding to the input key. The CPU 211 is a calculation processing unit that performs various types of calculations by sequentially executing the programmed command. The memory 212 stores various types of information according to the execution of the program of the CPU 211. The interface unit 216 is a site for receiving measurement result data (FIG. 5) or the like by the body composition monitor 100, and is configured by a slot to which the recording medium 132 can be attached and the peripheral circuit for controlling the slot in the present embodiment. In place of the slot to which the recording medium 132 can be attached, the interface unit may be configured as the communication interface unit capable of data communication with the body composition monitor 100. The fixed disc 213 is a non-volatile storage device for storing the program executed by the CPU 211, the various types of tables for determination (whole body evaluation table 1401, site evaluation table 1402, distribution table 1403), the measurement result data received from the body composition monitor 100, and the physical information of the user. Other output devices such as a printer may be connected to the information processing device 200 as needed.

The CPU 211 executes the measurement result output process, that is, the process corresponding to steps S16 to S24 of FIG. 8 based on the various types of tables and measurement result data stored in the fixed disc 213.

The program according to the present embodiment may be for calling the necessary module at a predetermined timing in a predetermined array and executing the process of the program modules provided as one part of the operating system (OS) of the computer. In this case, the relevant module is not included in the program itself and is operated cooperatively with the OS to execute the process. The program according to the present embodiment also includes such a program that does not include the module.

The program according to the present embodiment may be provided by being incorporated in one part of another program. In this case as well, the module included in another program is not included in the program itself and is operated cooperatively with the OS to execute the process. The program according to the present embodiment also includes such a program that is incorporated in another program.

The program product to be provided is installed in a program storage unit such as a hard disc, and executed. The program product includes the program itself and the storage medium in which the program is stored.

The embodiments disclosed herein are illustrative in all aspects and should not be construed as being restrictive. The scope of the present invention is defined by the claims rather than by the description made above, and all modifications equivalent in meaning with the claims and within the scope of the claims are intended to be encompassed herein.

Description of Symbols

1 upper limb unit
2 lower limb unit
3 cable
10*a* main body
10*b*, 10*c* grip
11 detection unit
12 control unit
13 timer
14 memory
15 display unit
16 operation unit
16A power supply button
16B memory button
16C measurement button
16D display switch button
16F left button
16G right button
16H 16I, 16J, 16K personal number button
17 power supply unit
18 communication unit
20 accommodating section
22 load sensor
41 physical information storage region
42 measurement result storage region
43 reference value storage region
44 body fat percentage table
45 muscle percentage table
100 body composition monitor 121 body composition calculating portion
122 ratio calculating portion
123 evaluation processing portion
124 display controlling portion
200 information processing device
210 information processing device main body
212 memory
213 fixed disc
214 FD drive device
215 CD-ROM drive device
216 interface unit
220 monitor
230 keyboard
240 mouse
E10 hand electrode
E20 foot electrode
E11, E12, E13, E14, E21, E22, E23, E24 electrode
1401 whole body evaluation table
1402 site evaluation table
1403 distribution table

The invention claimed is:

1. A body composition monitor comprising:
a plurality of electrodes configured to be brought into contact with a surface of a body of a user;
at least one processor;
at least one memory, the at least one memory storing instructions that when executed cause the at least one processor to perform as:
a first calculating portion configured to calculate a body composition value of a whole body and a body composition value by site of the user using the electrodes;
a second calculating portion configured to calculate a site ratio representing a ratio of the body composition value by site with respect to the body composition value of the whole body;
an evaluating portion configured to calculate a site evaluation index representing an evaluation index related to the calculated site ratio; and
an output processing portion configured to display information including the site evaluation index on a display unit; wherein
the site evaluation index includes a high and low level representing a height of the site ratio, and
the output processing portion is configured to display a schematic image of a human body on the display unit and also is configured to display a position in the human body image corresponding to a site where the calculated high and low level is higher than average or a site where the calculated high and low level is lower than average of the site so as to be identifiable from other positions.

2. The body composition monitor according to claim 1, wherein the output processing portion is configured to display on the display unit whole body information related to the body composition value of the whole body in association with the site evaluation index.

3. The body composition monitor according to claim 2, wherein the whole body information includes at least one of the body composition value of the whole body and an evaluation index of the body composition value of the whole body in a physical attribute including sex of the user.

4. The body composition monitor according to claim 1, wherein the output processing portion is configured to display the calculated site ratio on the display unit.

5. The body composition monitor according to claim 1, further comprising:
a non-transitory storage unit configured to store in advance specific information specifying a relationship of each high and low level representing a height of the site ratio and the site ratio for every physical attribute of a measurer, wherein
the evaluating portion is configured to calculate the high and low level corresponding to the calculated site ratio based on the specific information, the physical attribute of the user, and the calculated site ratio.

6. The body composition monitor according to claim 5, wherein the specific information includes at least one of a first table storing the high and low level targeting on all age attributes, and a second table storing the high and low level for every age attribute.

7. The body composition monitor according to claim 1, wherein
the site includes an arm, a body trunk, and a leg.

8. The body composition monitor according to claim 1, wherein
the evaluating portion is configured to calculate an age index indicating to which age attribute the calculated site ratio corresponds based on a distribution table representing a distribution of the site ratio for every age attribute, and the calculated site ratio as the site evaluation index.

9. The body composition monitor according to claim 1, further comprising:
a communication unit configured to transmit information of the calculated site ratio to a server, wherein
the communication unit is configured to receive information on a person with close balance of coverage of a body composition of the user from the server, and
the output processing portion is configured to display the information received by the communication unit on the display unit.

10. A non-transitory computer-readable storage medium causing a computer to execute a method for outputting a measurement result of a body composition including a display unit, the method comprising:
calculating a site ratio representing a ratio of a body composition value by site stored in the storage medium with respect to a body composition value of a whole body stored in the storage medium;
calculating a site evaluation index representing an evaluation index related to the calculated site ratio; and
displaying information including the site evaluation index on the display unit; wherein
the site evaluation index includes a high and low level representing a height of the site ratio, and
the displaying step includes displaying a schematic image of a human body and also displaying a position in the human body image corresponding to a site where the calculated high and low level is higher than average or a site where the calculated high and low level is lower than average of the site so as to be identifiable from other positions.

11. A non-transitory computer-readable storage medium causing a computer to execute a method for outputting a measurement result of a body composition; the method comprising:
calculating a site ratio representing a ratio of a body composition value by site with respect to a body composition value of a whole body;
calculating a site evaluation index representing an evaluation index related to the calculated site ratio; and
displaying information including the site evaluation index; wherein
the site evaluation index includes a high and low level representing a height of the site ratio, and the displaying step includes displaying a schematic image of a human body and also displaying a position in the human body image corresponding to a site where the calculated high and low level is higher than average or a site where the calculated high and low level is lower than average of the site so as to be identifiable from other positions.

* * * * *